(12) United States Patent
Nakanishi et al.

(10) Patent No.: US 7,763,741 B2
(45) Date of Patent: Jul. 27, 2010

(54) **SEPARATION OF GINKGOLIDES AND BILOBALIDE FROM *G. BILOBA***

(75) Inventors: Koji Nakanishi, New York, NY (US); Stanislav Jaracz, Trinec I (CZ); Shahid Malik, Edmonlón (CA); Hideki Ishii, New York, NY (US); Sergei V. Dzyuba, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 629 days.

(21) Appl. No.: 10/579,162

(22) PCT Filed: Nov. 9, 2004

(86) PCT No.: PCT/US2004/037412

§ 371 (c)(1),
(2), (4) Date: Sep. 5, 2007

(87) PCT Pub. No.: WO2005/046829

PCT Pub. Date: May 26, 2005

(65) Prior Publication Data

US 2008/0108837 A1    May 8, 2008

Related U.S. Application Data

(60) Provisional application No. 60/519,840, filed on Nov. 12, 2003.

(51) Int. Cl.
*C07D 407/00* (2006.01)
(52) U.S. Cl. .................................... 549/295
(58) Field of Classification Search .............. 549/297
See application file for complete search history.

(56) References Cited

U.S. PATENT DOCUMENTS

| | | |
|---|---|---|
| 4,981,688 A | 1/1991 | Ayroles et al. |
| 5,389,370 A | 2/1995 | O'Reilly et al. |
| 5,399,348 A | 3/1995 | Schwabe |
| 5,466,829 A | 11/1995 | Park et al. |
| 5,512,286 A | 4/1996 | Schwabe |
| 5,541,183 A | 7/1996 | Park et al. |
| 5,599,950 A | 2/1997 | Teng |
| 6,030,621 A | 2/2000 | De Long et al. |
| 6,117,431 A | 9/2000 | Ramazanov et al. |
| 6,143,725 A | 11/2000 | Vasella et al. |
| 6,174,531 B1 | 1/2001 | Zhang et al. |
| 6,187,314 B1 | 2/2001 | Xie et al. |
| 6,221,356 B1 | 4/2001 | Junsheng |
| 6,274,621 B1 | 8/2001 | Drieu |
| 6,328,999 B1 | 12/2001 | Schwabe |
| 6,590,109 B2 | 7/2003 | Lichtblau et al. |
| 6,693,091 B2 | 2/2004 | Stromgaad et al. |
| 6,844,451 B2 | 1/2005 | Lichtblau et al. |
| 7,145,021 B2 | 12/2006 | Stromgaard et al. |
| 2003/0194370 A1 | 10/2003 | Stromgaard et al. |
| 2003/0225052 A1 | 12/2003 | Stromgaard et al. |
| 2005/0119336 A1 | 6/2005 | Nakanashi et al. |
| 2005/0136136 A1 | 6/2005 | Lichtblau et al. |
| 2007/0098632 A1 | 5/2007 | Stromgaard et al. |

FOREIGN PATENT DOCUMENTS

| | | |
|---|---|---|
| DE | 21 17 429 | 10/1972 |
| GB | 2288559 A * | 4/1995 |
| GB | 2 228 599 | 11/1995 |
| WO | WO 93/02204 | 2/1993 |
| WO | WO 99/52911 | 10/1999 |
| WO | WO 02/083158 | 10/2002 |
| WO | WO 03/006040 | 1/2003 |
| WO | WO 03/082185 | 10/2003 |
| WO | WO 2005/021496 | 3/2005 |
| WO | WO 2005/046829 | 5/2005 |
| WO | WO 2005/092324 | 10/2005 |

(Continued)

OTHER PUBLICATIONS

U.S. Appl. No. 11/634,429, filed Dec. 5, 2006, Stromgaard et al.

(Continued)

*Primary Examiner*—D. Margaret Seaman
*Assistant Examiner*—Nizal S Chandrakumar
(74) *Attorney, Agent, or Firm*—John P. White; Cooper & Dunham LLP

(57) ABSTRACT

The subject invention provides a method for separating a terpene trilactone from Ginkgo biloba plant material or from an extract of Ginkgo biloba comprising a mixture of terpene trilactones, the process comprising the steps of:

Figure 1:
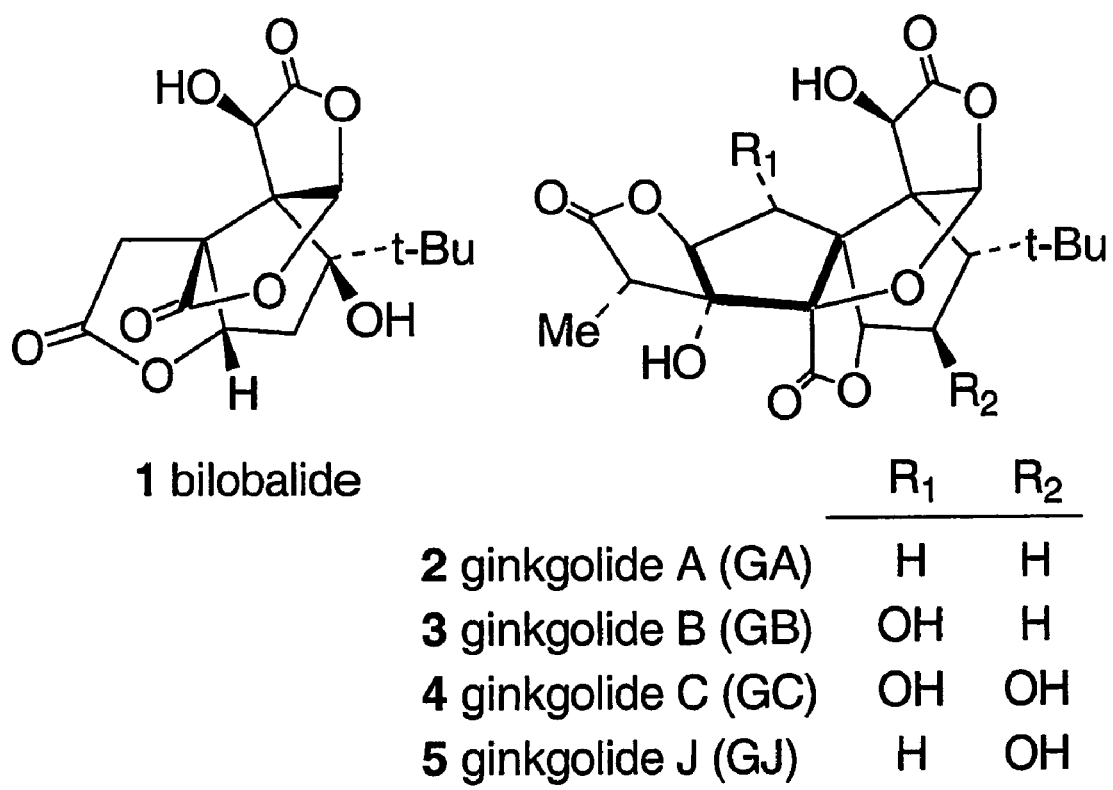

a) subjecting the Ginkgo biloba plant material or the extract to column chromatography with an appropriate solvent system to produce at least a first fraction containing the terpene trilactone bilobalide, a second fraction eluted after the first fraction containing the terpene trilactones GA and GB, and a third fraction eluted after the second fraction containing at least a preponderance of the terpene trilactones GC and GJ; and b) alkylating the terpene trilactone GB of the second fraction so as to produce a first mixture including terpene trilactone GA and alkylated terpene trilactone GB; or alkylating the terpene trilactone GC of the third fraction so as produce a second mixture including terpene trilactone GJ and alkylated terpene trilactone GC, so as to thereby isolate a terpene trilactone.

21 Claims, 5 Drawing Sheets

FOREIGN PATENT DOCUMENTS

| WO | WO 2006/083366 | 8/2006 |
|---|---|---|
| WO | WO 2007/002410 | 1/2007 |

OTHER PUBLICATIONS

Ahlemeyer, B. et al., "Pharmacological Studies Supporting The Therapeutic Use of *Ginkgo biloba* Extract For Alzheimer's Disease", *PMID*: 13130383 (2003).

Corey, E.J. & Su, W.G., "Total Synthesis of a C15 *Ginkgolide, bilobalide*", *J. Am. Chem. Soc.*, 1987, 109, 7534-7536.

Corey, E.J. et al., "Total Synthesis of *Ginkgolide bilobalide*", *J. Am. Chem. Soc.*, 1988, 110, 649-651.

Corey, E.J. & Ghosh, A.K., "Total Synthesis of Ginkgolide A" *Tetrahedron Lett.*, 1988, 29, 3205-3206.

Corey, E.J. & Gavai, A.V., "Simple Analogs of Ginkglolide B Which Are Highly Active Antagonists of Platelet Activating Factor", *Tetrahedron Lett.*, 1989, 30, 6959-6962.

Corey, E.J. et al., "Enantioselective Total Synthesis of Ginkgolide Derivatives Lacking the Tert-Butyl Group, an Essential Structural Subunit for Antagonism of Platelet Activating Factor", *Tetrahedron Lett.*, 1991, 32, 4623-4626.

Hu, L. et al., "Chemistry of Ginkgolides: Structure-Activity Relationship As PAF Antagonists", *Pure Appl. Chem.*, 1999, 71, 1153-1156.

Hu, L. et al., "Alkyl and Alkoxycarbonyl Derivatives of Ginkgolide B: Synthesis and Biological Evaluation of PAF Inhibitory Activity", *Bioorg. Med. Chem.*, 2000, 8, 1515-1521.

Hu, L. et al., "New Products From Alkali Fusion of Ginkgolides A and B", *J. Asian Nat. Prod. Res.*, 2000, 2, 103-110.

Hu, L. et al., "Synthesis and Biological Activity of Amide Derivatives of Ginkgolide A", *J. Asian Nat. Prod. Res.*, 2001, 3, 219-227.

Jaracz et al.; "Ginkgolides: Selective Acetylations, Translactonization, and Biological Evaluation", *J. Org. Chem.*, 2002, 67 (13): 4623-4626.

Lang, Q. et al. (2001) "Selective dissolution and one step separation of terpene trilactones in ginkgo leaf extracts for GC-FID determination," *Talanta* 54: 673-680.

McKenna, DJ et al., "Efficacy, safety, and use of *Ginkgo biloba* in clinical and preclinical applications", *PMID* 11565403, 2003.

Supplementary European Search Report issued Sep. 30, 2005 in connection with Application No. 02748132.4.

International Search Report issued Sep. 12, 2002 in connection with PCT/US02/22101.

International Search Report issued on Sep. 2, 2003 in connection with Application No. PCT/US03/12651.

International Search Report issued Mar. 17, 2005 in connection with Application No. PCT/US04/27671.

International Search Report issued Jan. 3, 2007 in connection with Application No. PCT/US06/24492.

International Preliminary Examination Report issued Apr. 21, 2003 in connection with PCT/US02/22101.

Tanaka, K. et al. (2005) "Unique Reactivity of α-Alkoxy Ginkgolide Lactones to Nucleophilic Reagents: Preparation of New Lactol Derivatives", Bull. Chem. Soc. Jpn., 78:1843-1850.

Tanaka, K. et al. (2005) "Preparation of Ginkgolide and F-seco-ginkgolide Lactols: the Unique Reactivity of α-hydroxy Lactones toward NaBH4", Tetrahedron Letters, 46:531-534.

Vogensen, S.B. et al. (2003) "Preparation of 7-Substituted Ginkgolide Derivatives: Potent Platelet Activating Factor (PAF) Receptor Antogonists", J. Med. Chem., 46:601-608.

International Search Report issued on Mar. 22, 2007 in connection with PCT/US05/42647.

Written Opinion of the International Searching Authority issued on Mar. 22, 2007 in connection with PCT/US05/42647.

International Search Report issued by the International Searching Authority (ISA/US) on Jun. 8, 2005 in connection with International Application No. PCT/US2004/037412.

Written Opinion of the International Searching Authority issued by the International Searching Authority (ISA/US) on Jun. 8, 2005 in connection with International Application No. PCT/US2004/037412.

Non-final Office Action issued Jan. 6, 2006 in connection with U.S. Appl. No. 10/925,209.

Non-final Office Action issued Apr. 24, 2006 in connection with U.S. Appl. No. 10/925,209.

Non-final Office Action issued Oct. 17, 2006 in connection with U.S. Appl. No. 10/925,209.

Non-final Office Action issued Aug. 2, 2007 in connection with U.S. Appl. No. 10/925,209.

Final Office Action issued Jan. 10, 2008 in connection with U.S. Appl. No. 10/925,209.

Notice of Allowance issued May 22, 2008 in connection with U.S. Appl. No. 10/925,209.

International Preliminary Examination Report issued on May 30, 2007 in connection with PCT/US2005/042647.

Office Action issued Nov. 14, 2007 in connection with U.S. Appl. No. 11/634,429.

Notification Concerning Transmittal of International Preliminary Report on Patentability issued Jan. 10, 2008 in connection with PCT/US2006/024492.

International Preliminary Examination Report issued on Apr. 21, 2003 in connection with PCT/US02/22101.

\* cited by examiner

1 bilobalide

| | $R_1$ | $R_2$ |
|---|---|---|
| 2 ginkgolide A (GA) | H | H |
| 3 ginkgolide B (GB) | OH | H |
| 4 ginkgolide C (GC) | OH | OH |
| 5 ginkgolide J (GJ) | H | OH |

FIGURE 3

R₁ = -H (GB)
R₁ = -OH (GC)

[Structure] + R-Br, K₂CO₃, DMF → [Product structure]

| Reaction conditions: | alkyl halide (10eq.) | K₂CO₃ (10eq.) | DMF, 0.5 – 10 h, r.t. |
|---|---|---|---|
| R | ratio 10-O/1-O in GC[a] | separation of the mixture[b] | deprotection method |
| benzyloxymethyl- | 1.4 : 1[c] | + | H₂, Pd/C, 1 atm |
| benzyl- | 14 : 1 | ++ | H₂, Pd/C, 4 atm |
| p-MeO-benzyl- | 20 : 1 | – – | CAN or H₂, Pd/C, 1 atm |
| allyl- | 5 : 1 | – – | 1) t-BuOK, 100°C; 2) 0.1 N-HCl, reflux |
| cinnamyl- | 5 : 1 | – – | 1) t-BuOK, 100°C; 2) 0.1 N-HCl, reflux |

[a] ratios for GB were similar or better;
[b] + = good, - = bad;
[c] (Corey, 1992)

Compound 8 - no reaction.

SEPARATION OF GINKGOLIDES AND BILOBALIDE FROM G. BILOBA

This application is a §371 national stage of PCT International Application No. PCT/US 2004/037412, filed Nov. 9, 2004, and claims the benefit of U.S. provisional application no. 60/519,840, filed Nov. 12, 2003, the contents of all of which are hereby incorporated by reference into this application.

This invention has been made with government support under National Institutes of Health grant AI10187. Accordingly, the U.S. Government has certain rights in the invention.

Throughout this application various publications are referenced in parenthesis. The disclosures of these publications in their entireties are hereby incorporated by reference into this application in order to more fully describe the state of the art to which this invention pertains.

This invention has been made with the government support under National Institutes of Health grant AI10187. Accordingly, the U.S. Government has certain rights in the invention.

Throughout this application various publications are referenced in parenthesis. The disclosures of these publications in their entireties are hereby incorporated by reference into this application in order to more fully describe the state of the art to which this invention pertains.

BACKGROUND OF THE INVENTION

The Ginkgo biloba tree mentioned in the Chinese Materia Medica 5000 years ago (Deng, Q. *Drug Use Perspective* 1988, 1, 57-58) has gained wide interest for its biological activities, especially in the treatment of memory related afflictions. Standardized extract EGb761 (Drieu, K.; Jaggy, H. in *Ginkgo biloba;* van Beek, T. A., Ed.; Harwood Academic Publishers: Amsterdam, 2000; Vol. 12, pp 267-277) from G. biloba leaves is a complex mixture containing flavonoids (22-24%) and terpene trilactones (TTL, 5-7%), and is one of the best selling herbal medicines (Schmid, W. *Nature* (London) 1997, 386, 755). The structures of ginkgolides A, B, and C were determined in 1967 (FIG. 1), (Nakanishi, K: *Pure Appl. Chem.* 1967, 14, 89-113; Okabe, K.; Yamada, K.; Yamamura, S.; Takada, S. *J. Chem. Soc. C* 1967, 2201-2206) while those of ginkgolide J (Weinges, K.; Hepp, M.; Jaggy, H. *Liebigs Ann. Chem.* 1987, 521-526) and bilobalide (Nakanishi, K.; Habaguchi, K.; Nakadaira, Y.; Woods, M. C.; Maruyama, M.; Major, R. T.; Alauddin, M.; Patel, A. R.; Weinges, K.; Bahr, W. *J. Am. Chem. Soc.* 1971, 93, 3544-3546) were elucidated later. Flavonoids and TTLs are believed to be associated with most of the pharmacological properties of G. biloba extracts. While flavonoids can be obtained from many other plants, ginkgolides and bilobalide are unique components of G. biloba extracts. They have attracted scientists to investigate the biological activity and putative link of these compounds to pharmacological activities of EGb761, particularly those related to neuromodulation (long term potentiation, cognitive symptoms of dementia) (MacLennan, K. M.; Darlington, C. L.; Smith, P. F. *Progress in Neurobiology* (Oxford, United Kingdom) 2002, 67, 235-257). Ginkgolides are well known for their platelet activating factor antagonistic activity (Braquet, P. *Drugs of the Future* 1987, 12, 643-699) and recently also for the selective inhibition of glycine receptors(Kondratskaya, E. L.; Krishtal, O. A. *Neurophysiology (Translation of Neirofiziologiya)* 2002, 34, 155-157). Although bilobalide lacks these activities its neuroprotective properties have been reported(Zhou, L. J.; Zhu, X. Z. *J. Pharmacol. Exp. Ther.* 2000, 293, 982-988; Janssens, D.; Remacle, J.; Drieu, K.; Michiels, C. *Biochem. Pharmacol.* 1999, 58, 109-119; Chandrasekaran, K.; Mahrabian, Z.; Spinnewyn, B.; Drieu, K.; Fiskum, G. *Brain Research* 2001, 922, 282-292). Recently, methods for the extraction of TTLs with organic solvents(PCT International Application No. WO 02/083158, published Oct. 24, 2002 (Teng, B. P.)), water (Lichtblau, D.; Berger, J. M.; Nakanishi, K. *Journal of Natural Products* 2002, 65, 1501-1504; U.S. Pat. No. 6,590,109, issued Jul. 8, 2003 to Lichtblau, et al.)), pressurized water (U.S. Pat. No. 6,524,628, issued Feb. 25, 2003 to Wai, et al.) or supercritical fluids (Choi, Y. H.; Kim, J.; Yoo, K. P. *Chromatographia* 2002, 56, 753-757; van Beek, T. A.; Taylor, L. T. *Phytochemical Analysis* 1996, 7, 185-191) have been developed. The individual terpene components can be separated from these enriched extracts by a 10-15 step fractional recrystalization (Nakanishi, K. *Pure Appl. Chem.* 1967, 14, 89-113; Okabe, K.; Yamada, K.; Yamamura, S.; Takada, S. *J. Chem. Soc. C* 1967, 2201-2206; Zhao, J.; Muhammad, I.; Dunbar, D. C.; Khan, I. A.; Fischer, N. H.; Fronczek, F. R. *Acta Crystallagraphica, Section C.: Crystal Structure Communications* 2002, C58, o195-o198; Dupont, L.; Dideberg, O.; Germain, G.; Braquet, P. *Acta Cryst.* 1986, C42, 1759-1762; Sbit, M.; Dupont, L.; Dideberg, O.; Braquet, P. *Acta Cryst.* 1987, C43, 2377-2381) repeated column chromatography (Weinges, K.; Bahr, W. *Liebigs Ann. Chem.* 1972, 759, 158-172), reversed-phase HPLC (Wada, K.; Sasaki, K.; Miura, K.; Yagi, M.; Kubota, Y.; Matsumoto, T.; Haga, M. *Biological and Pharmaceutical Bulletin* 1993, 16, 210-212; Lobstein-Guth, A.; Briancon-Scheid, F.; Anton, R. *Journal of Chromatography* 1983, 267, 431-438; Camponovo, F. F.; Wolfender, J. L.; Maillard, M. P.; Potterat, O.; Hostettmann, K. *Phytochemical Analysis* 1995, 6, 141-148, chromatography system with sephadex LH-20 (Teng, B. P. In *Ginkgolides—Chemistry, Biology, Pharmacology;* Braquet, P., Ed.; J. R. Prous Science Publishers, S. A., 1988, pp 37-42) or less problematically by chromatography on NaOAc impregnated silica gel (van Beek, T. A.; Lelyveld, G. P. *J. Nat. Prod.* 1997, 60, 735-738).

In contrast to the large number of methods in which the separation procedure is rather complicated or the individual terpene trilactones can only be obtained in low purity and/or low quality, described herein are simple and efficient separation methods for the separation of five terpene trilactones from G. biloba extract by a combination of benzylation, chromatography, and hydrogenolysis or a combination of extraction, chromatography and crystallization. Of particular importance for large-scale isolation of ginkgolides as phytopharmaceuticals, the described method enables separation without resorting to preparative reversed-phase HPLC or other expensive procedures.

SUMMARY OF THE INVENTION

The subject invention provides a process for separating a terpene trilactone from Ginkgo biloba plant material or from an extract of Ginkgo biloba comprising a mixture of terpene trilactones, the process comprising the steps of:

a) subjecting the Ginkgo biloba plant material or the extract to column chromatography with an appropriate solvent system to produce at least a first fraction containing the terpene trilactone bilobalide, a second fraction eluted after the first fraction containing the terpene trilactones GA and GB, and a third fraction eluted after the second fraction containing at least a preponderance of the terpene trilactones GC and GJ; and b) alkylating the terpene trilactone GB of the second fraction so as to produce a first mixture including terpene trilactone GA and alkylated terpene trilactone GB; or alkylating the terpene trilactone GC of the third fraction so as produce a second mixture including terpene trilactone GJ and alkylated terpene trilactone GC, so as to thereby isolate a terpene trilactone.

The invention also provides a process for separating a mixture of terpene trilactones GA and GB comprising the steps of:
  a) dissolving the mixture in a suitable solvent;
  b) adding benzyl bromide and a suitable base to the mixture, thereby preferentially benzylating terpene trilactone GB;
  c) separating benzylated terpene trilactone GB from terpene trilactone GA by column chromatography; and
  d) deprotecting benzylated terpene trilactone GB by catalytic hydrogenation.

The invention further provides a process for separating a mixture of terpene trilactones GC and GJ comprising the steps of:
  a) dissolving the mixture in a suitable solvent;
  b) adding benzyl bromide and a suitable base to the mixture, thereby preferentially benzylating terpene trilactone GC;
  c) separating benzylated terpene trilactone GC from terpene trilactone GJ by column chromatography; and
  d) deprotecting benzylated terpene trilactone GC by catalytic hydrogenation.

The invention also provides a process for separating a terpene trilactone from Ginkgo biloba plant material or an extract of Ginkgo biloba comprising a mixture of terpene trilactones, the process comprising the steps of:
  a) subjecting the Ginkgo biloba plant material or the extract to column chromatography with hexane/ethyl acetate to produce at least a first fraction containing the terpene trilactone bilobalide, a second fraction eluted after the first fraction containing the terpene trilactone GA and GB, and a third fraction eluted after the second fraction containing at least a preponderance of the terpene trilactones GC and GJ;
  b) rinsing the first fraction of step a) with ethyl ether to produce the terpene trilactone bilobalide in at least 98% purity;
  c) removing solvent under vacuum from the second fraction in step a) so as to produce a first residue containing at least a preponderance of terpene trilactones GA and GB; admixing the first residue in DMF with $K_2CO_3$ and benzyl bromide, thereby producing a first reaction mixture; quenching the first reaction mixture with HCl, thereby producing a first quenched product; extracting the first quenched product with ethyl acetate, thereby producing a first extracted product; and triturating the first extracted product with chloroform, thereby isolating the terpene trilactone GA in at least 98% purity and producing a filtrate;
  d) concentrating the filtrate of step c) under vacuum to produce a concentrated filtrate; subjecting the concentrated filtrate to column chromatography with hexane/ethyl acetate, thereby separating benzylated terpene trilactone GB from residual terpene trilactone GA; deprotecting the separated terpene trilactone GB by catalytic hydrogenation, thereby obtaining terpene trilactone GB in at least 98% purity;
  e) removing solvent under vacuum from the third fraction of step a) so as to produce a second residue containing at least a preponderance of terpene trilactones GJ and GC; admixing the second residue in DMF with $K_2CO_3$ and benzyl bromide, thereby producing a second reaction mixture; quenching the second reaction mixture with HCl, thereby producing a second quenched product; extracting the second quenched product with ethyl acetate, thereby producing a second extracted product; subjecting the second extracted product to column chromatography with hexane/ethyl acetate, thereby separating benzylated terpene trilactone GC from terpene trilactone GJ, providing terpene trilactone GJ in at least 85% purity; recrystallizing terpene trilactone GJ with ethanol/water, thereby providing terpene trilactone GJ in at least 98% purity; and
  f) deprotecting the benzylated terpene trilactone GC of step e) by catalytic hydrogenation in ethanol, thereby obtaining terpene trilactone GC in at least 95% purity.

The invention also provides a process for obtaining terpene trilactones from Ginkgo biloba plant material or an extract of Ginkgo biloba comprising a mixture of terpene trilactones, the process comprising the steps of:
  a) extracting the Ginkgo biloba plant material or the Ginkgo biloba extract with a first suitable solvent to produce a first residue and a first filtrate; extracting the first filtrate with a second suitable solvent to produce a second residue and a second filtrate;
  b) subjecting the second filtrate to column chromatography with a first chromatography system to obtain Bilibalide;
  c) extracting the second residue with a third suitable solvent to obtain terpene trilactone Ginkgolide B (GB) and a third filtrate;
  d) subjecting the third filtrate to column chromatography with a second chromatography system to produce a first fraction containing terpene trilactone Ginkgolide A (GA) and GB and a second fraction containing terpene trilactone Ginkgolide C (GC) and terpene trilactone Ginkgolide J (GJ);
  e) subjecting the first fraction to iterative extractions with a fourth suitable solvent to separate GA and GB; and
  f) subjecting the second fraction to column chromatography with a third chromatography system to separate GC and GJ,
thereby obtaining terpene trilactones, Bilibalide, GA, GB, GC and GJ isolated from each other and from the Ginkgo biloba plant material or the extract of Ginkgo biloba.

The invention also provides a process for obtaining terpene trilactones from Ginkgo biloba plant material or an extract of Ginkgo biloba comprising a mixture of terpene trilactones, the process comprising the steps of:
  a) extracting the Ginkgo biloba plant material or the Ginkgo biloba extract with ethyl acetate to produce a first residue and a first filtrate;
  b) concentrating the first filtrate of step a) to produce a concentrated first filtrate; extracting the concentrated first filtrate with diethyl ether to produce a second residue and a second filtrate;
  c) concentrating the second filtrate of step b) to produce a second concentrated filtrate; subjecting the second concentrated filtrate to column chromatography with hexanes/ethyl acetate to produce a fraction containing the terpene trilactone Bilibalide;
  d) removing the solvent from the fraction of step c) thereby obtaining the terpene trilactone Bilibalide;
  e) admixing the second residue of step b) with methanol and filtering to produce a third filtrate and the terpene trilactone Ginkgolide B (GB);
  f) concentrating the third filtrate of step e) to produce a third concentrated filtrate; subjecting the third concentrated filtrate to column chromatography with hexanes/acetone to produce a first fraction containing a mixture of terpene trilactones Ginkgolide A (GA) and GB and a second fraction containing a mixture of terpene trilactones Ginkgolide C (GC) and Ginkgolide J (GJ);
  g) removing the solvent from the second fraction of step f) to produce a third residue; subjecting the third residue to column chromatography with diethyl ether/methanol to produce third fraction containing GC and a fourth fraction containing GJ;

h) removing the solvent from the third fraction of step g) to thereby obtain GC;

i) removing the solvent from the fourth fraction of step b) to thereby obtain GJ;

j) removing the solvent from the first fraction of step f) to produce a fourth residue; extracting the fourth residue with methanol to produce GB and a fourth filtrate;

k) concentrating the fourth filtrate of step j) to produce a fourth concentrated filtrate; admixing the fourth concentrated filtrate with methanol and filtering to produce a fifth residue, which residue is GB enriched and a fifth filtrate;

l) concentrating the fifth filtrate of step k) and to produce a fifth concentrated filtrate; admixing the fifth concentrated filtrate with methanol and filtering to produce an sixth residue, which is GA enriched and a sixth filtrate;

m) concentrating the sixth filtrate of step l) to produce a sixth concentrated filtrate; admixing the sixth concentrated filtrate with methanol and crystallizing to produce GA;

n) admixing the fifth residue of step k) and the sixth residue of step l) to produce a first residue mixture, which is enriched in GA and GB; admixing the first residue mixture with methanol and filtering to produce GB and a seventh filtrate;

o) concentrating the seventh filtrate of step m) to produce a seventh concentrated filtrate; admixing the seventh concentrated filtrate with methanol and filtering to produce an eighth residue, which contains GA and an eighth filtrate;

p) concentrating the eighth filtrate of step o) to produce a eighth concentrated filtrate; admixing the eighth concentrated filtrate with methonal and crystallizing to produce GA, q) collecting the GA from steps m), o), and p), thereby obtaining GA; and r) collecting the GB from steps e), j), and n), thereby obtaining GB, thereby obtaining terpene trilactones.

The invention also provides a process for separating each of Bilibalide, Ginkgolide A, (GA), Ginkgolide B, (GB), Ginkgolide C, (GC), and Ginkgolide J, (GJ) from a mixture of terpene trilactones (TTL), wherein the separation is achieved through non-covalent interaction with the mixture of TTLs.

The invention also provides a process for isolating bilibalide from a mixture of terpene trilactones (TTL) wherein the mixture comprises Bilibalide, Ginkgolide A, (GA), Ginkgolide B, (GB), Ginkgolide C, (GC), and Ginkgolide J, (GJ), the process comprising the steps of:

a) extracting the mixture of TTLs with diethyl ether solvent to produce a residue and a filtrate; and b) subjecting the filtrate to column chromatography with a hexanes/ethyl acetate solvent system to thereby isolate Bilibalide from the mixture of TTLs.

DETAILED DESCRIPTION OF THE FIGURES

FIG. 1. Bilobalide and Ginkgolides A, B, C, and J.

Figure 2:
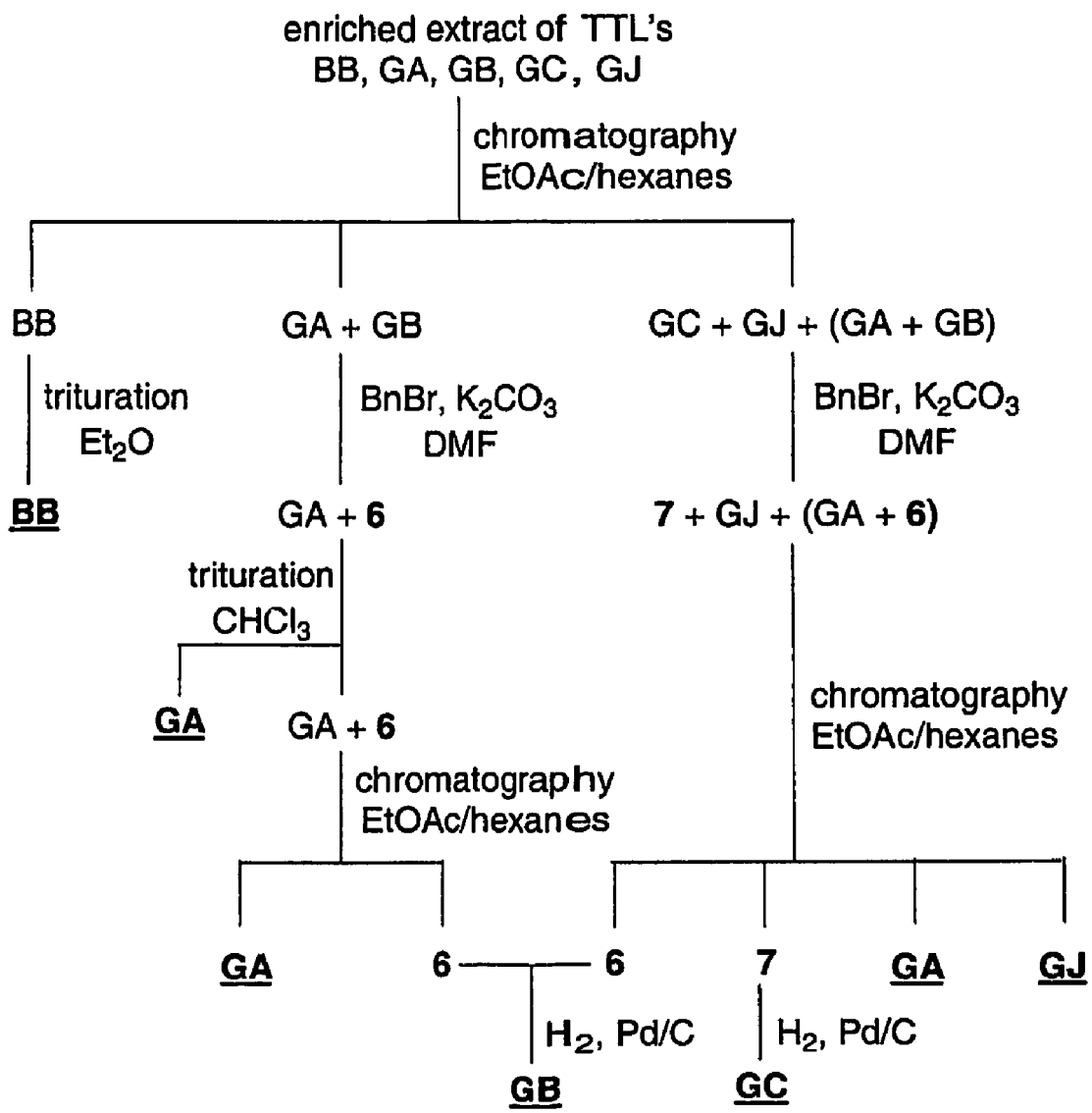

FIG. 2. Flow diagram showing the separation and isolation of terpene trilactones from enriched Ginkgo biloba extracts by a first method.

FIG. 3. Evaluation of different alkyl groups for selective alkylation of ginkgolides B and C.

Figure 4:
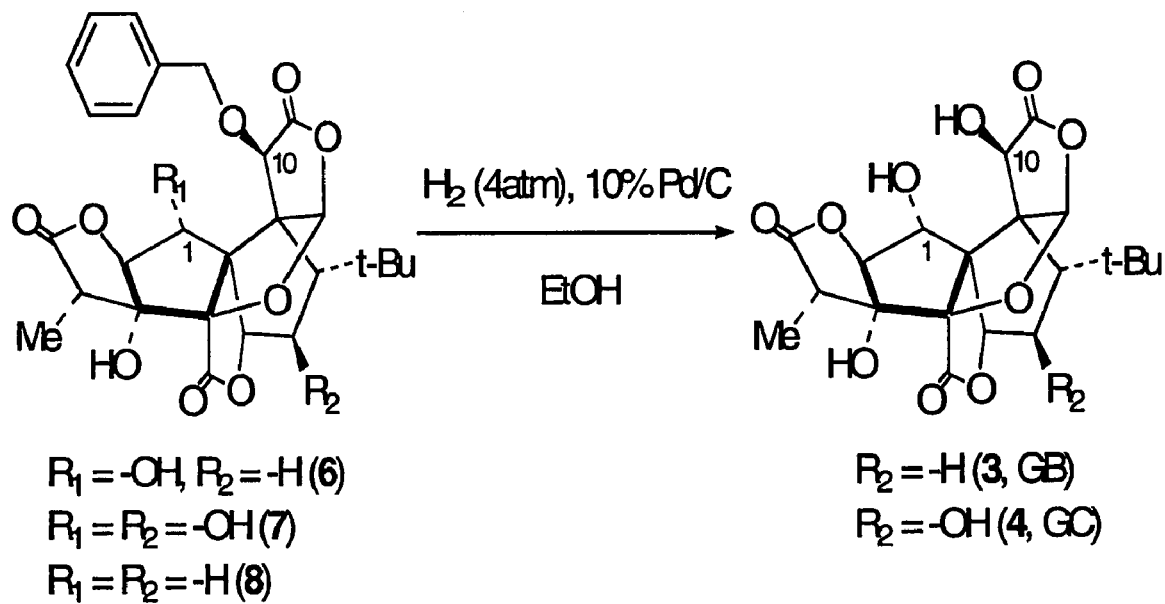

FIG. 4. Hydrogenolysis of benzylated ginkgolides B and C.

Figure 5:
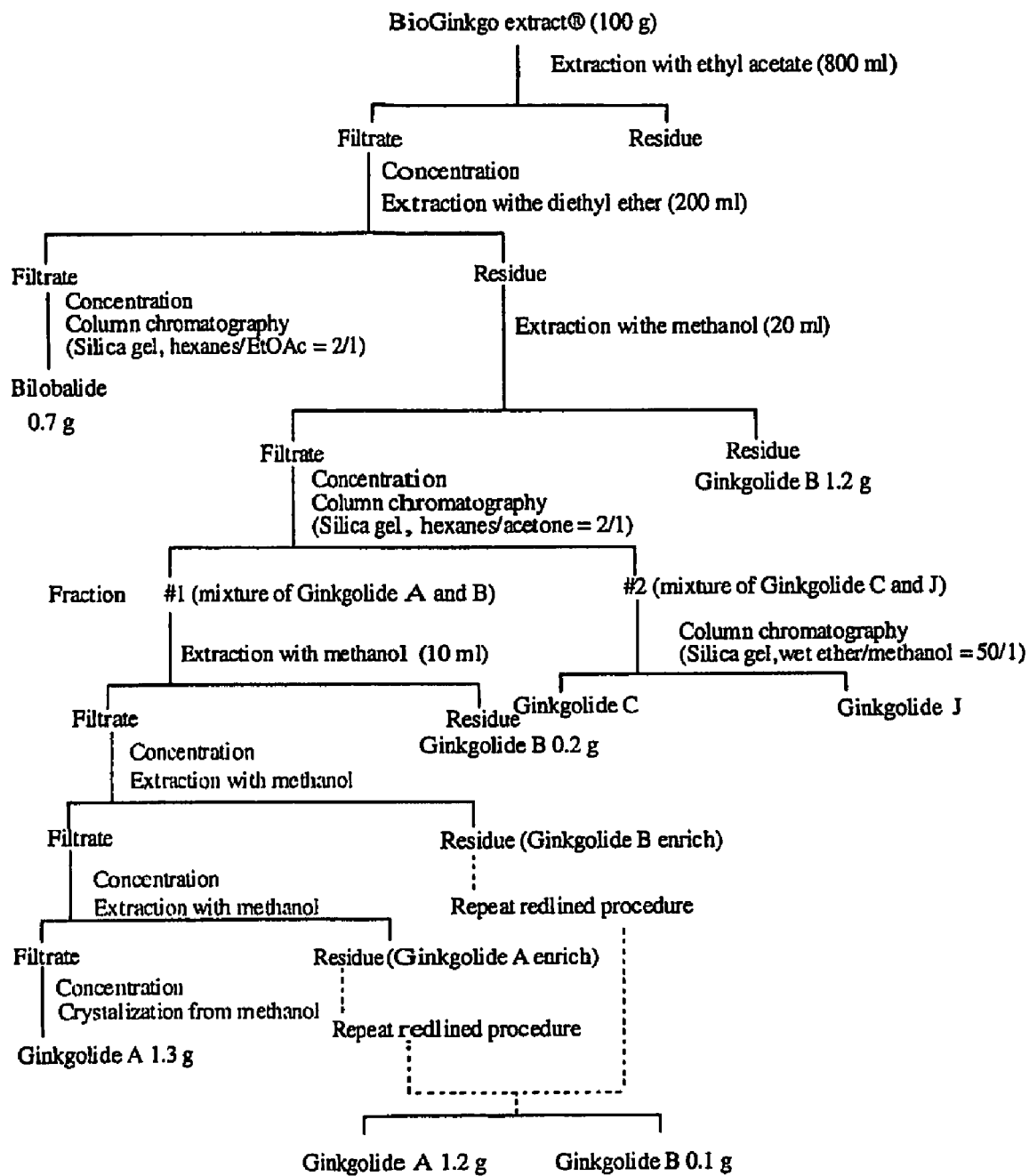

FIG. 5. Flow diagram showing the speration and isolation of terpene trilactones from Bioginkgo® 27/7 extract by a second method.

DETAILED DESCRIPTION OF THE INVENTION

The subject invention provides a process for separating a terpene trilactone from Ginkgo biloba plant material or from an extract of Ginkgo biloba comprising a mixture of terpene trilactones, the process comprising the steps of:

a) subjecting the Ginkgo biloba plant material or the extract to column chromatography with an appropriate solvent system to produce at least a first fraction containing the terpene trilactone bilobalide, a second fraction eluted after the first fraction containing the terpene trilactones GA and GB, and a third fraction eluted after the second fraction containing at least a preponderance of the terpene trilactones GC and GJ; and b) alkylating the terpene trilactone GB of the second fraction so as to produce a first mixture including terpene trilactone GA and alkylated terpene trilactone GB; or alkylating the terpene trilactone GC of the third fraction so as produce a second mixture including terpene trilactone GJ and alkylated terpene trilactone GC, so as to thereby isolate a terpene trilactone.

In one embodiment, in step a) of the process, the solvent system is hexane/ethyl acetate or petroleum ethers/ethyl acetate.

In another embodiment the process further comprises triturating the first fraction with a suitable solvent to produce the terpene trilactone bilobalide in at least 95% purity.

In yet another embodiment, the terpene trilactone bilobalide is produced in at least 98% purity.

In yet another embodiment, the suitable solvent is ethyl ether.

In a further embodiment, the alkylation of the terpene trilactone GB of the second fraction comprises the steps of:

a) removing solvent from the second fraction so as to produce a first residue containing at least a preponderance of terpene trilactones GA and GB;

b) admixing the first residue in a suitable polar solvent with a suitable base and R—Br, where R is a substituted or unsubstituted, straight-branched, or cyclic alkyl, or —$CH_{(2-5)}$—Ar, where Ar is an aromatic group, so as to produce a first reaction mixture;

c) quenching the first reaction mixture of step b) with a suitable acid;

d) extracting the product of step c) with a first suitable solvent so as to produce a composition comprising terpene trilactone GA and alkylated terpene trilactone GB; and e) triturating the product of step d) with a second suitable solvent, thereby isolating the terpene trilactone GA in at least 95% purity and producing a filtrate containing alkylated terpene trilactone GB.

In yet a further embodiment, in step e) of the process, the terpene trilactone GA is isolated in at least 98% purity.

In still yet a further embodiment of the process wherein the terpene trilactone GB of the second fraction is alkylated, in step a), the solvent is removed under vacuum;

in step b), the suitable polar solvent is DMF, the suitable base is $K_2CO_3$ or $Cs_2CO_3$, and R—Br is benzyl bromide;

in step c), the suitable acid is HCl;

in step d), the first suitable solvent is ethyl acetate; and in step e), the second suitable solvent is chloroform.

In another embodiment the process further comprises the steps of:

f) concentrating the filtrate of step e) under vacuum to produce a concentrated filtrate;

g) subjecting the concentrated filtrate to column chromatography with a suitable solvent system, thereby separating alkylated terpene trilactone GB from residual terpene trilactone GA; and h) deprotecting the alkylated terpene trilactone GB of step g) by catalytic hydrogenation, thereby obtaining the terpene trilactone GB in at least 95% purity.

In yet another embodiment, in step h) the terpene trilactone GB is obtained in least 98% purity.

In still yet another embodiment, the suitable solvent system in step g) is hexane/ethyl acetate or petroleum ethers/ethyl acetate.

In even yet another embodiment, the alkylation of the terpene trilactone GC of the third fraction comprises the steps of:

a) removing solvent from the third fraction so as to produce a second residue containing at least a preponderance of terpene trilactones GJ and GC;

b) admixing the second residue in a suitable polar solvent with a suitable base and R-Br,
where R is a substituted or unsubstituted, straight-chained or branched, or cyclic alkyl, or —$CH_{(2-5)}$—Ar,
where Ar is an aromatic group,
so as to produce a second reaction mixture;

c) quenching the second reaction mixture of step b) with a suitable acid;

d) extracting the product of step c) with a suitable solvent so as to produce a composition comprising terpene trilactone GJ and alkylated terpene trilactone GC;

e) subjecting the product of step d) to column chromatography with a first suitable solvent system, thereby separating alkylated terpene trilactone GC from terpene trilactone GJ, and providing terpene trilactone GJ in at least 85% purity; and f) recrystallizing terpene trilactone GJ from step e) with a second suitable solvent system, thereby providing terpene trilactone GJ in at least 95% purity.

In another embodiment of the alkylation of the terpene trilactone GC of the third fraction, in step a), the solvent is removed under vacuum;

in step b), the suitable polar solvent is DMF, the suitable base is $K_2CO_3$ or $Cs_2CO_3$, and R—Br is benzyl bromide;

in step c), the acid is HCl;

in step d), the solvent is ethyl acetate;

in step e), the first suitable solvent system is hexane/ethyl acetate or petroleum ethers/ethyl acetate; and in step f), the second suitable solvent system is ethanol/water.

In even yet another embodiment, the process comprises the step of deprotecting the alkylated terpene trilactone GC of the third fraction by catalytic hydrogenation in a suitable solvent, thereby obtaining the terpene trilactone GC in at least 95% purity.

In still yet another embodiment, the terpene trilactone GC is obtained in at least 98% purity.

In a further embodiment, the suitable solvent in the process for deprotecting the alkylated terpene trilactone GC of the third fraction is ethanol.

The invention further provides a composition comprising terpene trilactones GA and GB of step a) of the described process.

In another embodiment, the invention provides a composition comprising terpene trilactone GA and alkylated terpene trilactone GB of step d) of the process wherein terpene trilactone GB of the second fraction is alkylated.

In yet another embodiment, the invention yet further provides a composition comprising terpene trilactones GC and GJ of step a) of the process wherein terpene trilactone GC of the third fraction is alkylated.

In still yet another embodiment, invention even further provides a composition comprising alkylated terpene trilactone GC and terpene trilactone GJ present of step d) of the process wherein terpene trilactone GC of the third fraction is alkylated.

The invention also provides a product prepared by the process of step a) of the process wherein terpene trilactone GB of the second fraction is alkylated.

In a further embodiment, the invention provides a product prepared by step d) of the process wherein terpene trilactone GB of the second fraction is alkylated.

In still a further embodiment, the invention provides a product prepared by step a) of the process wherein terpene trilactone GC of the third fraction is alkylated.

In yet a further embodiment, the invention provides a product prepared by the step d) of the process wherein terpene trilactone GC of the third fraction is alkylated.

The invention also provides a process for separating a mixture of terpene trilactones GA and GB comprising the steps of:

a) dissolving the mixture in a suitable solvent;

b) adding benzyl bromide and a suitable base to the mixture, thereby preferentially benzylating terpene trilactone GB;

c) separating benzylated terpene trilactone GB from terpene trilactone GA by column chromatography; and d) deprotecting benzylated terpene trilactone GB by catalytic hydrogenation.

The invention also provides a process for separating a mixture of terpene trilactones GC and GJ comprising the steps of:

a) dissolving the mixture in a suitable solvent;

b) adding benzyl bromide and a suitable base to the mixture, thereby preferentially benzylating terpene trilactone GC;

c) separating benzylated terpene trilactone GC from terpene trilactone GJ by column chromatography; and d) deprotecting benzylated terpene trilactone GC by catalytic hydrogenation.

The invention also provides a process for separating a terpene trilactone from Ginkgo biloba plant material or an extract of Ginkgo biloba comprising a mixture of terpene trilactones, the process comprising the steps of:

a) subjecting the Ginkgo biloba plant material or the extract to column chromatography with hexane/ethyl acetate to produce at least a first fraction containing the terpene trilactone bilobalide, a second fraction eluted after the first fraction containing the terpene trilactone GA and GB, and a third fraction eluted after the second fraction containing at least a preponderance of the terpene trilactones GC and GJ;

b) rinsing the first fraction of step a) with ethyl ether to produce the terpene trilactone bilobalide in at least 98% purity;

c) removing solvent under vacuum from the second fraction in step a) so as to produce a first residue containing at least a preponderance of terpene trilactones GA and GB; admixing the first residue in DMF with $K_2CO_3$ and benzyl bromide, thereby producing a first reaction mixture; quenching the first reaction mixture with HCl, thereby producing a first quenched product; extracting the first quenched product with ethyl acetate, thereby producing a first extracted product; and triturating the first extracted product with chloroform, thereby isolating the terpene trilactone GA in at least 98% purity and producing a filtrate;

d) concentrating the filtrate of step c) under vacuum to produce a concentrated filtrate; subjecting the concentrated filtrate to column chromatography with hexane/ethyl acetate, thereby separating benzylated terpene trilactone GB from residual terpene trilactone GA; deprotecting the separated terpene trilactone GB by catalytic hydrogenation, thereby obtaining terpene trilactone GB in at least 98% purity;

e) removing solvent under vacuum from the third fraction of step a) so as to produce a second residue containing at least a preponderance of terpene trilactones GJ and GC; admixing the second residue in DMF with $K_2CO_3$ and benzyl bromide, thereby producing a second reaction mixture; quenching the second reaction mixture with HCl, thereby producing a second quenched product; extracting the second quenched product with ethyl acetate, thereby producing a second extracted product; subjecting the second extracted product to column chromatography with hexane/ethyl acetate, thereby separating benzylated terpene trilactone GC from terpene trilactone GJ, providing terpene trilactone GJ in at least 85% purity; recrystallizing terpene trilactone GJ with ethanol/water, thereby providing terpene trilactone GJ in at least 98% purity; and f) deprotecting the benzylated terpene trilactone GC of step e) by catalytic hydrogenation in ethanol, thereby obtaining terpene trilactone GC in at least 95% purity.

In yet another embodiment, the invention provides a process wherein terpene trilactone GJ in step g) is provided in at least 90% purity.

In still another embodiment, the invention provides a process wherein terpene trilactone GC in step f) is obtained in at least 98% purity.

The invention also provides a process for obtaining terpene trilactones from Ginkgo biloba plant material or an extract of Ginkgo biloba comprising a mixture of terpene trilactones, the process comprising the steps of:

a) extracting the Ginkgo biloba plant material or the Ginkgo biloba extract with a first suitable solvent to produce a first residue and a first filtrate; extracting the first filtrate with a second suitable solvent to produce a second residue and a second filtrate;

b) subjecting the second filtrate to column chromatography with a first chromatography system to obtain Bilibalide;

c) extracting the second residue with a third suitable solvent to obtain terpene trilactone Ginkgolide B (GB) and a third filtrate;

d) subjecting the third filtrate to column chromatography with a second chromatography system to produce a first fraction containing terpene trilactone Ginkgolide A (GA) and GB and a second fraction containing terpene trilactone Ginkgolide C (GC) and terpene trilactone Ginkgolide J (GJ);

e) subjecting the first fraction to iterative extractions with a fourth suitable solvent to separate GA and GB; and f) subjecting the second fraction to column chromatography with a third chromatography system to separate GC and GJ, thereby obtaining terpene trilactones, Bilibalide, GA, GB, GC and GJ isolated from each other and from the Ginkgo biloba plant material or the extract of Ginkgo biloba.

In another embodiment, the first suitable solvent is ethyl acetate.

In yet another embodiment, the second suitable solvent is diethyl ether.

In still another embodiment, the third suitable solvent is methanol.

In another embodiment, the fourth suitable solvent is methanol.

In another embodiment, the first chromatography system comprises hexanes/ethyl acetate.

In another embodiment, the second chromatography system comprises hexanes/acetone.

In yet another embodiment, the second chromatography system comprises diethyl ether/methanol.

In still another embodiment, subjecting the second filtrate to chromatography comprises the steps of:

a) concentrating the second filtrate to produce a second concentrated filtrate;

b) subjecting the second concentrated filtrate to column chromatography with hexanes/ethyl acetate to produce a fraction containing the terpene trilactone Bilibalide; and c) removing the solvent from the fraction of step b) thereby obtaining the terpene trilactone Bilibalide.

In another embodiment, subjecting the third filtrate to chromatography comprises the steps of:

a) concentrating the third filtrate to produce a third concentrated filtrate; and b) subjecting the third concentrated filtrate to column chromatography with hexanes/acetone to produce a first fraction containing a mixture of terpene trilactones Ginkgolide A (GA) and GB and a second fraction containing a mixture of terpene trilactones Ginkgolide C (GC) and Ginkgolide J (GJ).

In yet another embodiment, extracting the fraction containing a mixture of GA and GB with a fourth suitable solvent to obtain GA and GB comprises the steps of:

a) removing the solvent from the fraction to produce a residue;

b) extracting the residue of step a) with methanol to produce a filtrate and GB;

c) concentrating the filtrate of step b) to produce a concentrated filtrate of step b); admixing the concentrated filtrate of step b) with methanol and filtering to produce a GB enriched residue and a filtrate;

d) concentrating the filtrate of step c) to produce a concentrated filtrate of step c); admixing the concentrated filtrate of step c) with methanol and filtering to produce a GA enriched residue and a filtrate;

e) concentrating the filtrate of step d) to produce a concentrated filtrate of step d); admixing the concentrated filtrate of step d) with methanol and crystallizing to produce GA;

f) admixing the GB enriched residue of step c) and the GA residue of step d) to produce a first residue mixture, which is enriched in GA and GB; admixing the first residue mixture with methanol and filtering to produce GB and a filtrate;

g) concentrating the filtrate of step f) to produce a concentrated filtrate of step f); admixing the concentrated filtrate of step f) with methanol and filtering to produce GA and a filtrate;

h) concentrating the filtrate of step g) to produce a concentrated filtrate of step g); admixing the concentrated filtrate of step g) with methanol and crystallizing to produce GA, i) collecting GA from steps e), g), and h), thereby obtaining GA; and j) collecting the terpene trilacton GB from steps b), and f), thereby obtaining GB.

In another embodiment, subjecting the fraction containing GC and GJ to chromatography comprises the steps of:

a) concentrating the fraction to produce a concentrated fraction;

b) subjecting the concentrated fraction to column chromatography with diethyl ether/methanol to produce a GC containing fraction and a GJ containing fraction;

c) removing the solvent from the GC containing fraction thereby obtaining GC; and d) removing the solvent from the GJ containing fraction thereby obtaining GJ.

The invention also provides a process for obtaining terpene trilactones from Ginkgo biloba plant material or an extract of Ginkgo biloba comprising a mixture of terpene trilactones, the process comprising the steps of:

a) extracting the Ginkgo biloba plant material or the Ginkgo biloba extract with ethyl acetate to produce a first residue and a first filtrate;

b) concentrating the first filtrate of step a) to produce a concentrated first filtrate; extracting the concentrated first filtrate with diethyl ether to produce a second residue and a second filtrate;

c) concentrating the second filtrate of step b) to produce a second concentrated filtrate; subjecting the second concentrated filtrate to column chromatography with hexanes/ethyl acetate to produce a fraction containing the terpene trilactone Bilibalide;

d) removing the solvent from the fraction of step c) thereby obtaining the terpene trilactone Bilibalide;

e) admixing the second residue of step b) with methanol and filtering to produce a third filtrate and the terpene trilactone Ginkgolide B (GB);

f) concentrating the third filtrate of step e) to produce a third concentrated filtrate; subjecting the third concentrated filtrate to column chromatography with hexanes/acetone to produce a first fraction containing a mixture of terpene trilactones Ginkgolide A (GA) and GB and a second fraction containing a mixture of terpene trilactones Ginkgolide C (GC) and Ginkgolide J (GJ);

g) removing the solvent from the second fraction of step f) to produce a third residue; subjecting the third residue to column chromatography with diethyl ether/methanol to produce third fraction containing GC and a fourth fraction containing GJ;

h) removing the solvent from the third fraction of step g) to thereby obtain GC;

i) removing the solvent from the fourth fraction of step b) to thereby obtain GJ;

j) removing the solvent from the first fraction of step f) to produce a fourth residue; extracting the fourth residue with methanol to produce GB and a fourth filtrate;

k) concentrating the fourth filtrate of step j) to produce a fourth concentrated filtrate; admixing the fourth concentrated filtrate with methanol and filtering to produce a fifth residue, which residue is GB enriched and a fifth filtrate;

l) concentrating the fifth filtrate of step k) and to produce a fifth concentrated filtrate; admixing the fifth concentrated filtrate with methanol and filtering to produce an sixth residue, which is GA enriched and a sixth filtrate;

m) concentrating the sixth filtrate of step l) to produce a sixth concentrated filtrate; admixing the sixth concentrated filtrate with methanol and crystallizing to produce GA;

n) admixing the fifth residue of step k) and the sixth residue of step 1) to produce a first residue mixture, which is enriched in GA and GB; admixing the first residue mixture with methanol and filtering to produce GB and a seventh filtrate;

o) concentrating the seventh filtrate of step m) to produce a seventh concentrated filtrate; admixing the seventh concentrated filtrate with methanol and filtering to produce an eighth residue, which contains GA and an eighth filtrate;

p) concentrating the eighth filtrate of step o) to produce a eighth concentrated filtrate; admixing the eighth concentrated filtrate with methonal and crystallizing to produce GA, q) collecting the GA from steps m), o), and p), thereby obtaining GA; and r) collecting the GB from steps e), j), and n), thereby obtaining GB, thereby obtaining terpene trilactones.

The invention also provides a process for separating each of Bilibalide, Ginkgolide A, (GA), Ginkgolide B, (GB), Ginkgolide C, (GC), and Ginkgolide J, (GJ) from a mixture of terpene trilactones (TTL), wherein the separation is achieved through non-covalent interaction with the mixture of TTLs.

The invention also provides a process for isolating bilibalide from a mixture of terpene trilactones (TTL) wherein the mixture comprises Bilibalide, Ginkgolide A, (GA), Ginkgolide B, (GB), Ginkgolide C, (GC), and Ginkgolide J, (GJ), the process comprising the steps of:

a) extracting the mixture of TTLs with diethyl ether solvent to produce a residue and a filtrate; and b) subjecting the filtrate to column chromatography with a hexanes/ethyl acetate solvent system to thereby isolate Bilibalide from the mixture of TTLs.

Experimental Details

In the following examples, the invention is described in detail. The examples describe a method for isolating five terpene trilactones from G. biloba. The terpene trilactones were each isolated in high purity. Besides providing each terpene trilactone in higher purity and higher yield, the disclosed method involves a minimum of steps.

General Experimental Procedures

Reactions were monitored by analytical TLC with silica gel 60 $F_{254}$ and spots were visualized by heating and 254 nm irradiation. Column chromatography was performed using silica gel (230-400 mesh). $^1$H-NMR spectra were recorded on Bruker (300, 400 or 500 MHz) spectrometers. Purity was estimated from $^1$H-NMR spectra. Mass spectra were measured on JEOL JMS-HX110/100A HF mass spectrometer under FAB conditions with NBA as the matrix.

Extract Material

Enriched extract was prepared according to the method disclosed in U.S. patent application Ser. No. 6,590,109 starting with Bioginkgo 27/7 extract (Pharmanex, Provo, Utah). All other reagents were purchased and used as received.

EXAMPLE 1

Chromatography of Enriched G. biloba Extract. The enriched extract (4.0 g) in minimum amount of EtOAc was loaded on a silica gel (100 g) column. The column was slowly eluted with EtOAc/hexanes solvent mixtures either with or without slight external pressure. The initial solvent system was EtOAc/hexanes (3.5:6.5, 500 mL). Content of EtOAc in the eluent was increased gradually in six steps (4:6, 500 mL; 4.5:5.5, 500 mL; 5:5, 500 mL; 5.5:4.5, 500 mL; 6:4, 400 mL; 6.5:3.5, 400 mL). Content of the collected fractions was analyzed by TLC, and if necessary, was also analyzed by $^1$H-NMR. The fractions collected at 45% EtOAc/hexanes contained bilobalide (0.4 g). The fractions collected at 50% EtOAc/hexanes contained small amounts of impure BB and GA then mixture GA/GB. The fractions collected at 55% EtOAc/hexanes contained mixture GA/GB (1.1 g). The fractions collected at 60% EtOAc/hexanes contained mixture of GC/GJ (0.4 g) with small amount of GA and GB.

EXAMPLE 2

Purification of bilobalide. Bilobalide (310 mg) from the chromatography above was suspended in 2 mL of ethyl ether, filtered and washed twice with 1 mL of ethyl ether to yield 217 mg of bilobalide as a white powder (purity by $^1$H-NMR≧98%).

EXAMPLE 3

Benzylation of a mixture GA/GB. To a ginkgolide mixture from the above chromatography, (1.08 g, GB ~25% w/w, 0.63 mmol of GB; GA ~74% w/w) was added $K_2CO_3$ (879 mg, 6.3 mmol, 10 eq.) and DMF (11 mL). While stirring, benzyl bromide (756 mL, 6.3 mmol, 10 eq.) was added. The mixture was stirred for 40 minutes, then quenched with 1M HCl (18 mL) and the solution was extracted with EtOAc (3×) and dried with $MgSO_4$. Volatiles were removed under reduced pressure and/or by multiple azeotropic evaporations with chloroform. The product mixture was suspended in chloroform (10 mL), filtered and washed twice with chloroform (4 mL and 2 mL) to obtain 605 mg of GA (2) as a white powder (purity by $^1$H-NMR≧98%). The filtrate was concentrated and purified by gradient column chromatography (30-50% EtOAc/hexanes) to obtain 326 mg of 6 and 134 mg of GA (2). GA from the chromatography was further purified by recrystalization (EtOH/$H_2O$). All analytical data as previously reported (Roumestand, C.; Perly, B.; Hosford, D. J.; Braquet, P. *Tetrahedron* 1989, 45, 1975-1989).

EXAMPLE 4

Benzylation of a mixture GA/GB/GC/GJ. To a ginkgolide mixture (543 mg, GA~3%, GB~4.5%, GC~68%, GJ~21% w/w, 0.92 mmol of GB+GC) was added $K_2CO_3$ (1.27 g, 9.2 mmol, 10 eq.) and DMF (18 mL). While stirring, benzyl bromide (1.09 mL, 9.2 mmol, 10 eq.) was added. The mixture was stirred for 2 hours then quenched with 1M HCl (30 mL) and the solution was extracted with EtOAc (3×) and dried with $MgSO_4$. Volatiles were removed under reduced pressure and by multiple azeotropic evaporations with chloroform. The mixture was purified by gradient column chromatography (30-60% EtOAc/hexanes) to obtain 31.2 mg of 6, 407.7 mg of 7, 18.6 mg of GA (2) and 111 mg of GJ (5). GA and GJ were further purified by recrystalization from EtOH/$H_2O$. All analytical data as previously reported (Roumestand, C.; Perly, B.; Hosford, D. J.; Braquet, P. *Tetrahedron* 1989, 45, 1975-1989; Hu, L.; Chen, Z.; Xie, Y.; Jiang, H.; Zhen, H. *Bioorg. Med. Chem.* 2000, 8, 1515-1521; Vogensen, S. B.; Stromgaard, K.; Shindou, H.; Jaracz, S.; Suehiro, M.; Ishii, S.; Shimizu, T.; Nakanishi, K. *Journal of Medicinal Chemistry* 2003, 46, 601-608).

EXAMPLE 5

Hydrogenation of 6. To a solution of 6 (322 mg, 0.626 mmol) in EtOH (5 mL) in a thick-wall flask was added 10% Pd/C (64 mg) and the mixture was vigorously stirred under $H_2$ (56 psi, 3.8 atm). After 24 hours, the reaction mixture was filtered through celite. Volatiles were removed under reduced pressure to obtain 257 mg of ginkgolide B as a slightly brownish crystaline powder (97% yield). All analytical data as previously reported (purity by $^1$H-NMR≧98%) (Roumestand, C.; Perly, B.; Hosford, D. J.; Braquet, P. *Tetrahedron* 1989, 45, 1975-1989).

EXAMPLE 6

Hydrogenation of 7: To a solution of 7 (153 mg, 0.288 mmol) in EtOH (4 mL) in a thick-wall flask was added 10% Pd/C (31 mg) and the mixture was vigorously stirred under $H_2$ (56 psi, 3.8 atm). After 20 hours, the reaction mixture was filtered through celite. Volatiles were removed under reduced pressure. The product was washed with 15% EtOAc/hexanes (2×5 mL) to obtain 121.7 mg (96% yield) of GC (4) as a white powder. All analytical data as previously reported (purity by $^1$H-NMR≧98%) (Roumestand, C.; Perly, B.; Hosford, D. J.; Braquet, P. *Tetrahedron* 1989, 45, 1975-1989).

RESULTS

An efficient and rapid protocol has been developed for separation of individual ginkgolides and bilobalide from Ginkgo Biloba extracts. The procedure takes advantage of the enhanced susceptibility for benzylation that exists in ginkgolides B and C, contrasted with the unreactivity of ginkgolides A and J. The protocol is applicable to enriched extracts prepared from Ginkgo Biloba leaves as described previously (U.S. Pat. No. 6,590,109, issued Jul. 8, 2003 to Lichtblau, et al.). Bilobalide is separated by a single chromatography prior to benzylation. After derivatization, the ginkgolides are separated by a single column chromatography, and ginkgolides B and C are obtained from their benzylated derivatives by hydrogenolysis.

In 1992, Corey converted ginkgolides B and C which were in a mixture with ginkgolide A to benzyloxymethyl ethers, separated them by column chromatography and removed the protecting group by hydrogenolysis (Corey, E. J.; Rao, K. S.; Ghosh, A. K. *Tetrahedron Lett.* 1992, 33, 6955-6958). Only ginkgolides B and C undergo etherification because of the presence of 1-OH, which stabilizes the alkoxy anion from 10-OH by hydrogen bonding. The method described herein is a gram-scale protocol in which the individual ginkgolides A/B/C/J and bilobalide are isolated and purified rapidly and efficiently from a crude G. biloba extract by a combination of benzylation, chromatography, and hydrogenolysis (FIG. 2).

Initially, the enriched extract (Lichtblau, D., Berger, J. M.; Nakanishi, K. *Journal of Natural Products* 2002, 65, 1501-1504) (53% TTLs) was subjected to a column chromatography on silica gel, with EtOAc/hexanes as a solvent system for elution (gradient, 35-65% EtOAc/hexanes) either with or without slight external pressure. This chromatography is necessary because bilobalide is unstable in conditions used during alkylation. Bilobalide thus obtained was already ~90% pure. Trituration with ethyl ether provided pure bilobalide (>98%) as a white powder. Surprisingly, the single column chromatography also yielded a nearly baseline separation of ginkgolide pairs GA/GB and GC/GJ with dramatically reduced content of flavonoids and other components of the extract. The later pair contained also small amounts of GA and GB.

Several alkyl groups for selective alkylation of GB/GC in the presence of GA/GJ were studied (FIG. 3). Interestingly, reaction with allyl bromide or cinnamyl bromide lead to partial alkylation of GA (2). However, the 10-alkyl-GA derivatives could not be separated from the 10-alkyl-GB derivatives. Benzyl bromide reacted with GA very slowly and no product could be detected with the first 90 minutes. Therefore, benzylation was selected for further consideration since GA/GJ do not react, while an excellent separation of benzyl ginkgolides 10-Bn-GB, 6 and 10-Bn-GC, 7 from unreacted GA/GJ is achieved on silica gel, and the benzyl groups can be readily removed by hydrogenolysis on Pd/C.

Of the bases we tested, the best results were obtained by using $K_2CO_3$ and $Cs_2CO_3$ as base; $Na_2CO_3$ and $Et_3N$ lead to incomplete conversion while stronger bases such as alkali hydrides or LDA lead to decomposition and a complex mixture of products. Of the solvents we tested, DMF was the best solvent because of quantitative conversions and no side reactions. The benzylation in other polar solvents such as acetone, acetonitrile and methanol lead to lower yields forming various side products, which could not be removed by chromatography. Increase in temperature or reaction time to more than 3 hours lead to formation of 10-Bn-GA (8), which is inseparable from 10-Bn-GB (6). Since benzyl derivatives are soluble in halogenated hydrocarbons, mixture of 10-Bn-GB (6) and GA (2) could be separated by trituration with chloroform. Ginkgolide A thus obtained as a white powder had purity of >98%. The filtrate, rich in 10-Bn-GB (6), was further purified by column chromatography on silica gel to obtain pure 10-BnGB (6) and GA (2). The mixture after benzylation of GC/GJ (with traces of GA/GB) was separated directly by column chromatography to obtain 10-Bn-GB (6), 10-Bn-GC (7), GA (2) and GJ (5). Catalytic hydrogenation (10% Pd/C) of the benzyl ethers under 4 atm of $H_2$ effected quantitative deprotection in 24 h to obtain native GB (3) and GC (4) (FIG. 4). Interestingly, 10-Bn-GA (8) as the impurity in some samples of 10-Bn-GB (6), did not react under these conditions, therefore GB (3) was not contaminated by GA (2) and the purification was facile. It is likely that 1-OH in 10-Bn-GB (6) and 10-Bn-GC (7) coordinates to Pd during hydrogenation. This activation is not possible in the case of GA derivative (8) therefore Pd cannot reach the sterically hindered benzyl group. To obtain pure compounds, the ginkgolides were further recrystalized in some cases ($EtOH/H_2O$).

In conclusion, we have developed a simple and efficient method for isolation of five TTLs from G. biloba extracts on gram scale. Starting from enriched extracts with >50% of TTLs, only three column chromatographies suffices. Benzylation of the ginkgolides can be performed in reagent grade DMF on air. Trituration affords GA in excellent purity. All of this is possible without resorting to expensive preparative reversed-phase HPLC. This is of particular importance for large-scale isolation of ginkgolides as phytopharmaceuticals. Furthermore, 10-Bn-GC (7) is an ideal precursor for a wide variety of transformations including the transformation into GB (Corey, E. J.; Rao, K. S.; Ghosh, A. K. *Tetrahedron Lett.* 1992, 33, 6955-6958; Teng, B. P. in *Ger. Offen.*; (Societe De Conseils De Recherches Et D'applications Scientifiques (SCRAS), Fr.). De, 1992, p 6).

EXAMPLE 7

Isolation of Ginkgolides from Bioginkgo® 27/7 extract. As shown in FIG. 5, Bioginkgo® extract 27/7 (100 g) was extracted with EtOAc (800 ml). The EtOAc extract was evaporated to give 7.0 g of brown solid. This solid was washed with $Et_2O$ (200 ml). The $Et_2O$ extract was concentrated and purified by column chromatography ($SiO_2$, 100 g, hexanes-EtOAc, 2:1) to give Bilibalide (0.7 g). The residue was dissolved in MeOH (20 ml) and filtrated to give colorless powder of Ginkgolide B (1.2 g). The filtrate was concentrated and subjected to silica gel column chromatography ($SiO_2$, 500 g, hexanes-acetone, 2:1) to give fractions of GA/GB mixture (2.3 g) and GC/GJ mixture (0.5 g). The GC/GJ mixture was purified by column chromatography ($SiO_2$, 200 g, wet $Et_2O$—MeOH, 50:1) to give GC (0.4 g) and GJ (0.1 g). The GA/GB mixture was dissolved in MeOH and filtered to give GB (0.2 g) as a residue. The filtrate was concentrated and dissolved in MeOH, then filtered to give GB enriched residue. The filtrate was concentrated and dissolved in MeOH, then filtered to give GA enriched residue. The filtrate was crystalized with MeOH to give GA (1.3 g). The enriched GA and GB residues were combined and further purified by repeating the series of methanol extractions, filtrations and crystallizations to give GA (1.2 g) and GB (0.1 g), respectively.

RESULTS

This isolation of ginkgolides has been carried out using simple extraction, crystalization and silica gel column chromatography without chemical modification of ginkgolides or using of reverse phase column chromatography.

What is claimed is:

1. A process for separating a terpene trilactone from Ginkgo biloba plant material or from an extract of Ginkgo biloba comprising a mixture of terpene trilactones, the process comprising the steps of:
    a) subjecting the Ginkgo biloba plant material or the extract to column chromatography with an appropriate solvent system to produce at least a first fraction containing the terpene trilactone bilobalide, a second fraction eluted after the first fraction containing the terpene trilactones GA and GB, and a third fraction eluted after the second fraction containing at least a preponderance of the terpene trilactones GC and GJ; and
    b) alkylating the terpene trilactone GB of the second fraction so as to produce a first mixture including terpene trilactone GA and alkylated terpene trilactone GB; or alkylating the terpene trilactone GC of the third fraction so as produce a second mixture including terpene trilactone GJ and alkylated terpene trilactone GC, so as to thereby isolate a terpene trilactone.

2. The process of claim 1, wherein in step a), the solvent system is hexane/ethyl acetate or petroleum ethers/ethyl acetate.

3. The process of claim 1, further comprising triturating the first fraction with a suitable solvent to produce the terpene trilactone bilobalide in at least 95% purity.

4. The process of claim 3, wherein the terpene trilactone bilobalide is produced in at least 98% purity.

5. The process of claim 3, wherein the suitable solvent is ethyl ether.

6. The process of claim 1, wherein the alkylation of the terpene trilactone GB of the second fraction comprises the steps of:
    a) removing solvent from the second fraction so as to produce a first residue containing at least a preponderance of terpene trilactones GA and GB;
    b) admixing the first residue in a suitable polar solvent with a suitable base and R-Br,
        where R is a substituted or unsubstituted, straight-branched, or cyclic alkyl, or —$CH_{(2-5)}$—Ar,
        where Ar is an aromatic group,
    so as to produce a first reaction mixture;
    c) quenching the first reaction mixture of step b) with a suitable acid;
    d) extracting the product of step c) with a first suitable solvent so as to produce a composition comprising terpene trilactone GA and alkylated terpene trilactone GB; and
    e) triturating the product of step d) with a second suitable solvent, thereby isolating the terpene trilactone GA in at least 95% purity and producing a filtrate containing alkylated terpene trilactone GB.

7. The process of claim 6, wherein in step e) the terpene trilactone GA is isolated in at least 98% purity.

8. The process of claim 6,
    wherein in step a), the solvent is removed under vacuum;

wherein in step b), the suitable polar solvent is DMF, the suitable base is $K_2CO_3$ or $Cs_2CO_3$, and R—Br is benzyl bromide;

wherein in step c), the suitable acid is HCl;

wherein in step d), the first suitable solvent is ethyl acetate; and wherein in step e), the second suitable solvent is chloroform.

9. The process of claim 6, further comprising the steps of:

f) concentrating the filtrate of step e) under vacuum to produce a concentrated filtrate;

g) subjecting the concentrated filtrate to column chromatography with a suitable solvent system, thereby separating alkylated terpene trilactone GB from residual terpene trilactone GA; and h) deprotecting the alkylated terpene trilactone GB of step g) by catalytic hydrogenation, thereby obtaining the terpene trilactone GB in at least 95% purity.

10. The process of claim 9, wherein in step h) the terpene trilactone GB is obtained in least 98% purity.

11. The process of claim 9, wherein the suitable solvent system in step g) is hexane/ethyl acetate or petroleum ethers/ethyl acetate.

12. The process of claim 1, wherein the alkylation of the terpene trilactone GC of the third fraction comprises the steps of:

a) removing solvent from the third fraction so as to produce a second residue containing at least a preponderance of terpene trilactones GJ and GC;

b) admixing the second residue in a suitable polar solvent with a suitable base and R—Br, where R is a substituted or unsubstituted, straight-chained or branched, or cyclic alkyl, or —$CH_{(2-5)}$—Ar, where Ar is an aromatic group, so as to produce a second reaction mixture;

c) quenching the second reaction mixture of step b) with a suitable acid;

d) extracting the product of step c) with a suitable solvent so as to produce a composition comprising terpene trilactone GJ and alkylated terpene trilactone GC;

e) subjecting the product of step d) to column chromatography with a first suitable solvent system, thereby separating alkylated terpene trilactone GC from terpene trilactone GJ, and providing terpene trilactone GJ in at least 85% purity; and f) recrystallizing terpene trilactone GJ from step e) with a second suitable solvent system, thereby providing terpene trilactone GJ in at least 95% purity.

13. The process of claim 12, wherein in step a), the solvent is removed under vacuum;

wherein in step b), the suitable polar solvent is DMF, the suitable base is $K_2CO_3$ or $Cs_2CO_3$, and R—Br is benzyl bromide;

wherein in step c), the acid is HCl;

wherein in step d), the solvent is ethyl acetate;

wherein in step e), the first suitable solvent system is hexane/ethyl acetate or petroleum ethers/ethyl acetate; and wherein in step f), the second suitable solvent system is ethanol/water.

14. The process of claim 1, further comprising the step of deprotecting the alkylated terpene trilactone GC of the third fraction by catalytic hydrogenation in a suitable solvent, thereby obtaining the terpene trilactone GC in at least 95% purity.

15. The process of claim 14, wherein the terpene trilactone GC is obtained in at least 98% purity.

16. The process of claim 14, wherein the suitable solvent is ethanol.

17. A composition comprising terpene trilactone GA and alkylated terpene trilactone GB of step d) of claim 6.

18. A process for separating a mixture of terpene trilactones GC and GJ comprising the steps of:

a) dissolving the mixture in a suitable solvent;

b) adding benzyl bromide and a suitable base to the mixture, thereby preferentially benzylating terpene trilactone GC;

c) separating benzylated terpene trilactone GC from terpene trilactone GJ by column chromatography; and d) deprotecting benzylated terpene trilactone GC by catalytic hydrogenation.

19. A process for isolating a ginkgolide from a mixture of terpene trilactones (TTLs) that comprises ginkgolide A, ginkgolide J, ginkgolide C, and ginkgolide B comprising:

a) exposing the mixture of TTLs to $K_2CO_3$, in dimethylformamide;

b) adding benzyl-bromide to the product of step a);

c) quenching the product of step b) with HCl and extracting with EtOAc and drying with $MgSO_4$; and d) purifying the product of step c) with gradient column chromatography to produce a mixture comprising ginkgolide A and ginkgolide J.

20. The process of claim 19, further comprising purifying the ginkgolide A by recrystallizing from $EtOH/H_2O$.

21. The process of claim 19, further comprising purifying the ginkgolide J by recrystallizing from $EtOH/H_2O$.

* * * * *